United States Patent [19]
Levius

[11] Patent Number: 5,887,593
[45] Date of Patent: Mar. 30, 1999

[54] URINARY INCONTINENCE DEVICE

[76] Inventor: Dezso K. Levius, 409 Meadow La., Oldsmar, Fla. 34677

[21] Appl. No.: 970,280

[22] Filed: Nov. 14, 1997

Related U.S. Application Data

[60] Provisional application No. 60/036,218 Jan. 28, 1997.
[51] Int. Cl.[6] ...................................................... A61F 5/48
[52] U.S. Cl. .................................. 128/885; 128/DIG. 25; 600/29
[58] Field of Search ...................................... 128/885, 886, 128/DIG. 25; 600/29–31; 604/96

[56] References Cited

U.S. PATENT DOCUMENTS

| | | | |
|---|---|---|---|
| 5,114,398 | 5/1992 | Trick | 128/DIG. 25 |
| 5,131,906 | 7/1992 | Chen | 128/DIG. 25 |
| 5,140,999 | 8/1992 | Ardito | 128/885 |
| 5,234,409 | 8/1993 | Goldberg | 128/DIG. 25 |

*Primary Examiner*—Michael A. Brown
*Attorney, Agent, or Firm*—Workman, Nydegger, & Seeley

[57] ABSTRACT

A urinary incontinence device comprising a tubular insert having a free distal end and an opposing proximal end, the insert being configured to be received within the urethra of a patient and being sufficiently flexible to be collapsed under constriction of the urethra. A flange radially projects out from the proximal end of the insert and is configured to seal against the opening of the urethra. An expandable reservoir is attached to the flange on the opposing side of the insert. A fluid channel extends from an opening on the exterior of the insert to the reservoir.

22 Claims, 3 Drawing Sheets

URINARY INCONTINENCE DEVICE

BACKGROUND OF THE INVENTION

This application claims the benefit of U.S. provisional application Ser. No. 60/036,218, filed Jan. 28, 1997.

1. The Field of the Invention

The present invention relates to devices for controlling and regulating urinary incontinence in women.

2. Present State of the Art

Urinary incontinence in women is a relatively common problem which exists in three primary forms. Stress urinary incontinence occurs as a result of physical stress, such as Lifting, coughing, or sneezing. Urge urinary incontinence is a result of gradual loss of control of the nerves that control the micturition process. Mixed urinary incontinence is a combination of symptoms of stress urinary incontinence and urge urinary incontinence.

The problem is often a source of difficulty or embarrassment to the affected woman. One solution, in relatively mild cases, has been the use of pads or diapers to absorb the uncontrolled seepage of urine. This can be undesirable as it sometimes results in restricting the type or style of clothing wished to be worn, as well as requiring frequent changing of absorbent devices. Discomfort and irritation due to the lingering presence of captured urine against tender urogenital tissues is another problem existing with external absorbent systems.

More severe cases require the temporary use of an intraurethral device to control the involuntary seepage or flow of urine. Several devices are known in the prior art for dealing with the problems of urinary incontinence in women. One device comprises a relatively rigid valved catheter having an extendible sealing portion on the interior end of the catheter. The sealing portion must be relatively rigid as it secures the device in the patient and defines at least one aperture to allow the passage of urine into the device. A manually operable valve is located between the internal and external ends of the catheter to enable the woman to selectively control elimination of urine at desired places and times. Other types of valved devices are known, and these generally comprise rigid tubular casings with valves inserted at various locations.

Still other prior art devices comprise solid plugs which are inserted into the urethra to block the involuntary seepage or flow of urine. Several such devices are known in the prior art. As claimed in U.S. Pat. No. 5,082,006, one prior art device comprises a relatively thin, solid shaft having at least one knob or thickening of the shaft along its length. Another device, as claimed in U.S. Pat. No. 5,090,424, comprises a flexible urethral plug which has a soft molded inflatable plastic catheter and a transportable fluid. The device is inserted into the urethra. Pressure applied to an external bellow causes the fluid to be transported into the interior end of the device. The interior or distal end of the device increases in diameter as a result, securely implanting the plug on a temporary basis. Removal is accomplished by deflating the implanted plug.

Most devices employ some kind of enlargement of the interior end of the catheter or shaft to secure the device within the urethra following placement. This can result in discomfort to the woman, and may lead to a sensation of a necessity to void the bladder when it may not be necessary. Additionally, many women suffering from stress urinary incontinence have bladder necks and proximal urethras that will open up during a stress event. This condition exists when the bladder neck becomes deformed from its normally perpendicular state to one which sags downward. When this condition is encountered, securing of the device via an enlarged distal end within the urethra may be negatively affected due to the enlargement occurring at the wrong position on the device.

Further, many prior art devices utilize a form stable catheter or shaft which remains temporarily implanted in the urethra. As a result, the urethra will necessarily be deformed from its normally collapsed configuration which is naturally assumed at all times except during urination, when it will be open. Additional problems, such as bladder and urethral infections may also develop from the extended presence of a relatively rigid artificial body in the urethra, and associated open urethra. The insertion of the rigid device can also transfer bacteria to the bladder.

OBJECTS AND BRIEF SUMMARY OF THE INVENTION

Accordingly, it is an object of the present invention to provide improved devices for controlling incontinence in women.

Another object of the present invention is to provide improved devices which are relatively comfortable and enable women to live a substantially normal and active life.

Another object of the present invention is to provide improved devices which do not significantly deform the urethra or bladder neck.

Still another object of the present invention is to provide improved devices which capture urine involuntarily passing through the urethra.

Yet another object of the present invention is to provide improved devices which keep captured urine away from the urogenital tissues.

Finally, another object of the present invention is to provide improved devices which can be emptied of captured urine without having to remove the device.

To achieve the foregoing objects, and in accordance with the invention as embodied and broadly described herein a urinary incontinence device is provided. The device comprises a tubular insert having a free distal end, an opposing proximal end, and a channel longitudinally extending therebetween. An opening extends from the exterior to the channel at the proximal end of the insert. The insert is configured for being received within a urethra and is sufficiently flexible to be collapsed upon normal constriction of the urethra. A hydrogel coating is placed over the insert so as to make the insert slippery and thus easy to place within the urethra.

Radially projecting out from the proximal end of the insert is a flange. The flange is configured to seal against the urethra opening when the insert is within the urethra. An adhesive can be applied to the flange to both seal and secure the flange against the meatus. Mounted to the flange on the side opposite the insert is a reservoir tube bounding a chamber. The reservoir tube has a first end fluid coupled to the channel within the tubular insert and an opposing second end. The second end of the reservoir tube is flattened and coiled in a natural repose. As a result of this flattened and coiled configuration, fluid is prevented from freely flowing through the second end of the reservoir tube. A one way duck bill valve is positioned between the insert channel and the reservoir chamber so as to enable fluid to pass from the insert chamber to the reservoir chamber but preventing fluid from passing from the reservoir chamber to the insert channel.

The insert is positioned within the urethra such that the sealing flange having adhesive thereon is biased against the opening of the urethra. During a bout of incontinence, the sphincter muscle of the urethra expands allowing urine to flow into the urethra. The urine is prevented from passing through the urethra as a result of the sealing flange. The fluid thus enters into the channel of the insert through the opening thereof. As the sphincter muscle constricts, the insert collapses forcing the urine therein to pass through the duck bill valve and into the reservoir tube. In turn, the reservoir tube expands by uncoiling to accommodate the captured urine.

The inventive incontinence device has several advantages over the prior art designs. For example, the hydrogel coating makes the device easy and painless to insert. In addition, since the insert collapses so as to minimize the obstruction within the urethra, the patient experience only minimal discomfort. Furthermore, since the channel within the insert is collapsed by the urethra, there is no continual opening along the urethra, thereby decreasing the potential for infections. Finally, since the urine is collected within the reservoir, it is not subject to contact with the urogenital tissue.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
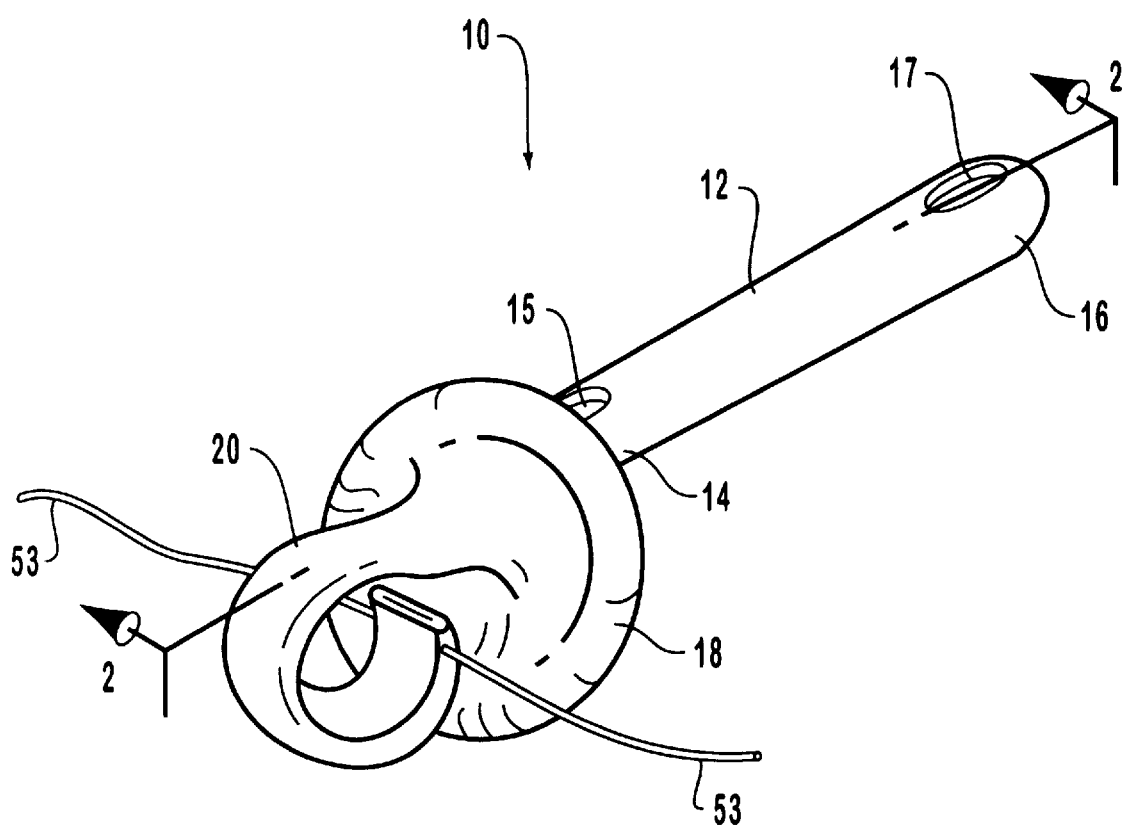
FIG. 1 is perspective view of the inventive device.

Depicted in FIG. 1 is one embodiment of a device 10 incorporating features of the present invention and being designed for controlling and regulating urinary incontinence in women. Device 10 generally comprises an elongated tubular insert 12 extending between a proximal end 14 and an opposing free distal end 16. A proximal opening 15 is formed at proximal end 14. Likewise, a distal opening 17 is formed at distal end 16. Radially projecting out from proximal end 14 of insert 12 is a flange 18. Projecting from flange 18 on the side opposite insert 12 is a coiled, reservoir tube 20. During use, insert 12 is positioned within the urethra of a patient so that flange 18 is biased against the opening thereof. During urinary incontinence, urine entering the urethra is blocked from passing therethrough by flange 18. As a result, the fluid passes into insert 12 through one of openings 15 or 17. The urine may subsequently flow into reservoir tube 20.

Figure 2:
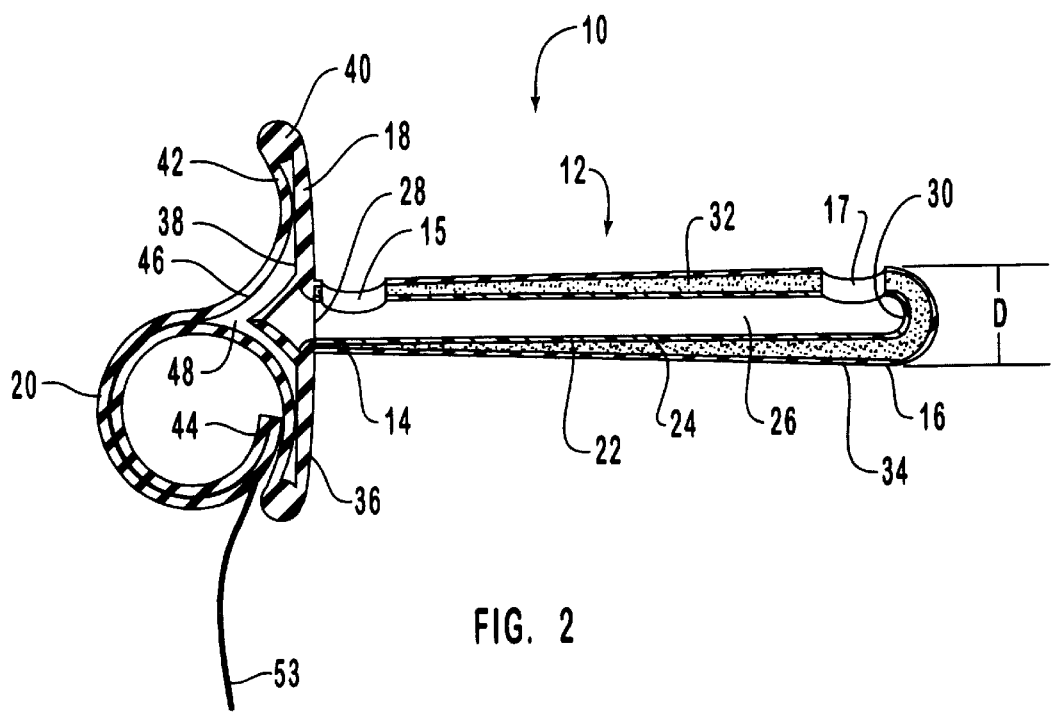
FIG. 2 is a cross-sectional side view of the inventive device shown in FIG. 1 taken along sections lines 2—2.

Depicted in FIG. 2, insert 12 comprises a flexible tube 22 longitudinally extending between proximal end 14 and distal end 16. Tube 22 has an interior surface 24 that bounds a channel 26 also extending between ends 14 and 16. Channel 26 has an opening 28 at proximal end 14 but is closed at a distal terminus 30. Each of openings 15 and 17 extend through tube 22 to communicate with channel 26. In alternative embodiments, a plurality of openings can extend through both ends 14 and 16. Furthermore, opening 17 at distal end 16 can be removed.

Tube 22 is preferably made of a material possessing the characteristics of good strength, flexibility, and biocompatibility. Tube 22 should be strong enough to withstand the stresses involved in insertion and withdrawal, as well as stresses imposed upon it by conventional use. In one embodiment of the present invention, tube 22 is sufficient flexible to be at least partially collapsed or flattened by the pressure exerted on it by normal constriction of a closed urethra. Specifically, in one embodiment, tube 22 is sufficiently flexible to be collapsed by the urethra sphincter muscle so that channel 26 is at least closed thereat when the urethra is closed. Tube 22 should also be sufficiently resilient to expand channel 26 open when the urethra is opened. Acceptable materials for tube 22 include, but are not limited to, polyurethane, silicone, C-Flex®, TecoFlex®, Tecothane®, and Telethane®.

Insert 12 further includes a foam layer 32 disposed over tube 22. Foam layer 32 is sufficiently flexible to be compressed by the normal internal pressure exerted by the urethra in the closed, non-urination configuration. Thus, following insertion of insert 12, foam layer 32 may compress in the urethra to conform as closely as possible to the normal shape of the urethra in the non-voiding state, giving maximum comfort. The foam is also space filling to prevent unwanted leakage of urine between insert 12 and the urethra wall.

Another function of foam layer 32 is that after insertion, the portion of foam layer 32 extending into the bladder neck is able to freely expand, thus automatically assuming the shape of the bladder neck. This phenomenon, in turn, provides several additional advantages. When dealing with stress incontinence, stresses are exerted on the bladder, causing inadvertent urination. The presence of expanded foam over a flexible tube within the bladder neck and assuming the shape of the bladder neck serves to reduce the effects of stress incontinence by absorbing abdominal pressure spikes during stress events. Such events include coughing, sneezing, and other vigorous physical activity. Additionally, the expanded foam creates a bottleneck effect, effectively enhancing sealing of device 10 and resisting the passage of urine through the urethra.

In one embodiment, foam layer 32 comprises an open-cell type foam, and may or may not exhibit some swelling due to absorption of ambient body moisture. Where foam materials exhibiting swelling characteristics are used, device 10 has improved retention characteristics following emplacement. Foam layer 32 should also remain sufficiently soft and flexible to provide patient comfort, as well as exhibiting good biocompatibility characteristics. Suitable foam materials include silicone, polyurethane, polyvinyl acetal polymer (PVA), and polyvinyl formyl sponge.

It is also contemplated that a surface layer 34 can be deposited over foam layer 32. Surface layer 32 can comprise an anti-microbial chemical agent such as chlorhexidine gluconate (CHG) or silver compounds to reduce the likelihood of infection during use. Additionally, materials such as hyaluronic acid, a hydrogel, or other materials may be deposited on foam layer 32 to mimic mucous. Surface layer 34 may also comprise a slip coat such as a hydrophilic hydrogel or a hydrophobic silicone to facilitate insertion and removal. It is envisioned that one or more of the above described surface layer materials can be used. Furthermore, rather then being deposited on foam layer 32, the above surface layer materials can mixed with or impregnated into foam layer 32.

It will be appreciated that a wide variation in urethral size exists in different women. Accordingly, insert 12 can be configured having an outer diameter D of different sizes. In one embodiment, it is contemplated that outer diameter D can be in a range between about 12 French (4.0 mm) to about 26 French (8.7 mm). It will be understood, however, that in unusual cases, this range may be exceeded in either direction. Therefore, the dimensional figures given are for purposes of illustration only and not intended to be limiting. To help maintain insert 12 within the urethra, outer diameter D can also vary along the length of insert 12. Specifically, diameter D can gradually increase from proximal end 14 to distal end 16.

The present invention also includes sealing means positioned at proximal end 14 of insert 12 for sealing the opening to the urethra closed when insert 12 is received within the urethra. By way of example and not by limitation, radially projecting out from proximal end 14 of insert 12 is flange 18. Flange 18 comprises an outer face 36 and an inner face 38 each projecting to an outer ring 40. Although optional, ring 40 help to stabilize flange 18 in an outwardly projecting position. Flange 18, including ring 40, is preferably made of a soft flexible material such as those previously discussed with regard to tube 22. Such materials include medical grade silicone or aliphatic polyurethane sold commercially under the name "TECOFLEX"®. It is further contemplated that an adhesive materials may be applied to outer face 36 of flange 18 to aid in securing the device after emplacement. Suitable adhesive materials include hydrogel and hydrocolloid materials.

The present invention also includes reservoir means attached to the sealing means on the side opposite insert 12 for holding fluid. By way of example and not by limitation, depicted in FIG. 2 is reservoir tube 20. Reservoir tube 20 has a first end 42 attached to ring 40 and an opposing free second end 44. An interior surface 46 bounds a chamber 48 within reservoir tube 20. Opening 28 extends through flange 28 to enable fluid communication between chamber 48 and channel 26. In alternative embodiments, the reservoir means can comprise a bag, balloon, or other flexible types of compartment structures.

Figure 3:
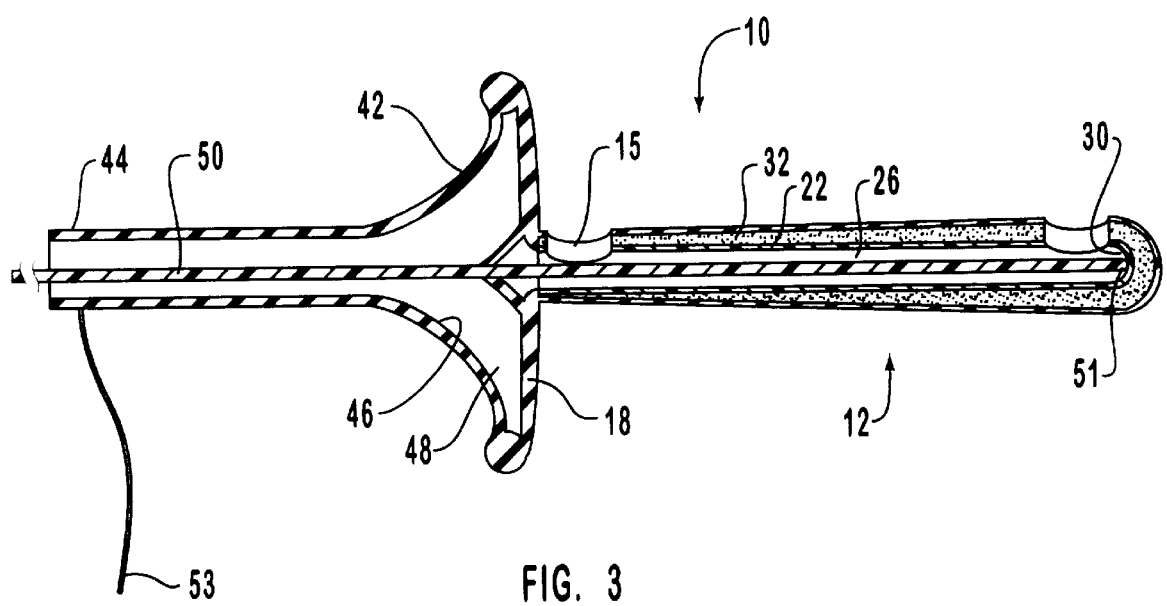
FIG. 3 is a cross-sectional side view of the device shown in FIG. 2 in an extended position.

The present invention further includes value means incorporated into reservoir tube 20 for selectively opening or closing external access chamber 48. By way of example and not by limitation, second end 44 of reservoir tube 20 is coiled and flattened in its natural state of repose. As a result, fluid is prevented from freely flowing therethrough. As fluid enters reservoir tube 20 from first end 42, the fluid pressure causes reservoir tube 20 to correspondingly expand and uncoil. Depicted in FIG. 3, reservoir tube 20 is in a fully expanded position. Due to the relatively low fluid pressures of the present use, reservoir tube 20 does not normally fully open as depicted in FIG. 3 unless manually extended. Reservoir tube 20 can, however, expand sufficiently to allow captured urine to flow out second end 44. Of course, it is preferred that chamber 48 be manually emptied before such leaking occurs. Once the captured urine is removed, reservoir tube 20 automatically retracts to its natural coiled position.

In alternative embodiments, valve means can include second end 44 of reservoir tube 20 simply being kinked or twisted so as to close off the opening thereat. In alternative embodiments, more conventional valve mechanisms can also be used. Reservoir tube 20 can be made out of the same flexible materials as previously discussed with regard to flange 18 and tube 22. However, by selectively varying the thickness and/or material properties, the pressure required to expand reservoir tube 20 can be varied.

In another embodiment of the present invention, means attached to reservoir tube 20 are provided for manually uncoiling reservoir tube 20. By way of example and not by limitation, as depicted in FIGS. 1–3, pull strings 49 attach to and project from the opposing sides of reservoir tube 20 at second end 44. By simply grabbing and pulling on pull strings 49, reservoir tube 20 uncoils to the expanded position. In alternative embodiments, pull strings 53 can be replaced by handles, rings, or other suitable structures for holding onto second end 44 of reservoir tube 20.

FIG. 3 shows device 10 with an introducer tool 50 in place and extending the length of the tube 22. Introducer tool 50 is comprised of a relatively stiff material such as nylon, and is of a smaller outer diameter than the inner diameter of the tube 22. The far distal end 51 of introducer tool 50 is rounded to minimize the likelihood of penetrating the closed distal terminus 30 during insertion. Device 10 is preferably sold sterilized with introducer tool 50 preloaded.

Figure 4:
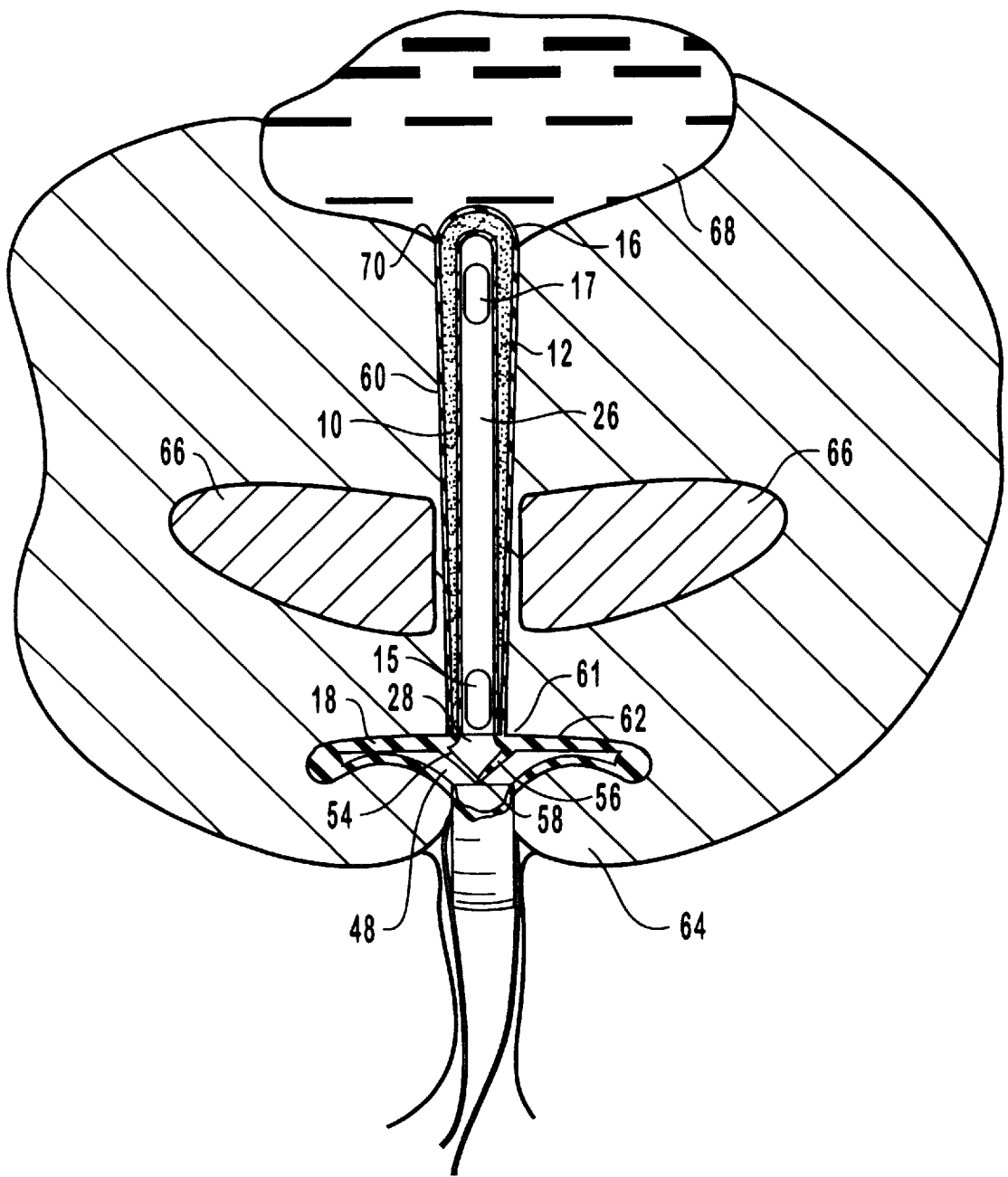
FIG. 4 is a partial cross-sectional top view of the device shown in FIG. 1 inserted within the urethra of a patient.

Insertion of device 10 can be done by the user. Device 10 is intended to be replaced on a daily basis. The patient first spreads or opens her labium major and labium minor to expose the urethral opening. As depicted in FIG. 4, device 10 is inserted into the patient's urethra 60 until the flange 18 rests against the vestibular floor or meatus 62. When device 10 is fully inserted, the labium major and labium minus 64 are allowed to close, covering flange 18, and firmly securing device 10 throughout the period of use. Following emplacement of device 10, insertion tool 50 is removed.

Once insert 12 is positioned within urethra 60, urethra sphincter muscle 66 constricts causing the wall of urethra 60 to compress against and collapse insert 12. Collapsing of insert 12 not only makes insert 12 more comfortable but also closes off channel 26, thereby preventing the passage of urine from bladder 68 through channel 26. In one embodiment, distal opening 17 is preferably positioned within urethra 60 as opposed to within bladder 68. Distal end 16 of insert 12 seals bladder neck 70 closed to also help prevent urine from entering channels 26 through distal opening 17.

During periods of incontinence, urethra sphincter muscle 66 relaxes enabling small amounts of urine to flow from bladder 66 into urethra 60 and also enabling radial expansion of insert 12. The urine is prevented from passing out through urethra opening 61 as a result of flange 18 being biased thereagainst. The urine thus remains within the urethra or passes into channel 26 through openings 15 or 17. As urethra sphincter muscle 66 again constricts closed, insert 12 is again collapsed. Since the maximum pressure point along the urethra is located at sphincter muscle 66, urine disposed between sphincter muscle 66 and bladder 68 is pushed back into bladder 68. In contrast, urine disposed between urethra sphincter muscle 66 and urethra opening 61 passes from channel 26 through opening 28 and into chamber 48 of reservoir tube 20. As the fluid enters reservoir 20, the fluid pressure causes reservoir tube 20 to expand to accommodate the fluid. The resilient nature of reservoir tube 20, however, produces a continual force against the urine located therein.

In one embodiment, fluid is permitted to freely flow between channel 26 and chamber 48 through opening 28. Accordingly, during a second bout of incontinence, the resistive pressure applied by reservoir tube 20 causes fluid therein to again pass into channel 26 as urethra 60 expands. This back flow of urine into channel 28 prevents additional urine from flowing from bladder 68 into channel 26.

In an alternative embodiment, one way valve means are provided for enabling fluid to travel from channel 26 to chamber 48 but preventing fluid from traveling from chamber 48 to channel 26. By way of example and not by limitation, depicted in FIGS. 2–4 is a duck bill valve 54. Duck bill valve 54 comprises a pair of lips 56 projecting from flange 18 on opposing sides of opening 28 into chamber 48. The distal ends of lips 56 bias together at a junction 58.

During use, as urethra 60 constricts closed, the urine is pushed against duck bill valve 54 causing lips 56 to separate at junction 58 and allowing the urine to pass into chamber 48. Once the urine passes therethrough, lips 56 bias closed again preventing the urine from passing back into channel 26. During subsequent bouts of urinary incontinence, the urine is continually accumulated into chamber 48. As more urine passes into chamber 48, reservoir tube 20 continues to expand. In this regard, reservoir tube 20 also functions as a sensor. That is, as reservoir tube 20 expands, the patient can feel the expansion, notifying the user that reservoir tube 20 is filling with urine.

To empty chamber 48 or when it is necessary for the patient to urinate, the patient locates and pulls pull strings 53, which may extend externally from the meatus, with one hand while securing device 10 with the other hand. By pulling string 53, reservoir tube 20 is expanded into the extended position allowing urine to pass therethrough. Following successful urination or emptying of chamber 48, pull string 53 are released allowing reservoir tube 20 to return to its natural closed position.

Removal of device 10 is accomplished by the patient spreading or opening her labia majora and labia minora, and simply withdrawing device 10. In the case of a thicker foam layer 32 at distal end 16 of device 10, the material is very soft and pliant, which allows any retained moisture to be easily squeezed out. Removal of the device, therefore, results in compression of the thickened foam on distal end 16, allowing easy removal.

In an alternative embodiment, device 10 can be formed and used without insert 12. In this embodiment, device 10 simply comprises flange 18 having reservoir tube 20 attached thereto. Opening 28 is exposed to the exterior and communicates with chamber 48 of reservoir tube 20. During use, flange 18 is sealed against meatus 62 so that opening 28 communicates with the urethra opening. As urine travels down the urethra, the urine is forced through opening 28, past duck bill valve 54, and into chamber 48.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A device for collecting involuntary urine flow through a urethra having an opening and a sphincter muscle, the device comprising:
    (a) an elongated insert having a free distal end and an opposing proximal end, the insert being configured for positioning within the urethra, the insert comprising a hollow insert tube and a foam layer deposited over the insert tube;
    (b) sealing means positioned at the proximal end of the insert for sealing the opening to the urethra closed when the insert is received within the urethra;
    (c) reservoir means attached to the sealing means on the side opposite the insert for holding fluid; and
    (d) a fluid passageway extending from the insert to the reservoir, the fluid passageway communicating with the exterior through an opening in the insert.

2. A device as recited in claim 1, further comprising one way valve means for enabling fluid to travel from the insert to reservoir means but preventing fluid from traveling from the reservoir means to the insert.

3. A device as recited in claim 1, wherein the opening in the insert is positioned between the urethra opening and the sphincter muscle when the insert is positioned within the urethra.

4. A device as recited in claim 1, wherein the sealing means comprises a flexible flange radially outwardly extending from the proximal end of the insert.

5. A device as recited in claim 1, wherein reservoir means comprises a reservoir tube having a chamber with a first end coupled to the fluid passageway.

6. A device as recited in claim 5, further comprising valve means for selectively opening or closing external access to the chamber of the reservoir tube.

7. A device as recited in claim 6, wherein the valve means comprises a second end of the reservoir tube being flattened and coiled.

8. A device as recited in claim 1, further comprising a hydrogel coating deposited over the foam layer.

9. A device as recited in claim 1, wherein the insert is sufficiently flexible to be collapsed under normal constriction of the urethra.

10. A device for collecting involuntary urine flow through a urethra having an opening and a sphincter muscle, the device comprising:
    (a) an insert tube having a free distal end, an opposing proximal end, and a channel extending therebetween, the channel communicating with the exterior through a first opening in the insert tube, the insert tube being configured for positioning within the urethra;
    (b) sealing means positioned at the proximal end of the insert tube for sealing the opening to the urethra closed when the insert tube is received within the urethra; and
    (c) an expandable reservoir attached to the sealing means on the side opposite the insert tube, the reservoir being in fluid communication with the channel in the insert tube.

11. A device as recited in claim 10, further comprising:
    (a) the first opening being positioned at the proximal end of the insert tube; and
    (b) a second opening positioned at the distal end of the insert tube.

12. A device as recited in claim 10, further comprising a layer of hydrophilic foam being disposed on the insert tube.

13. A device as recited in claim 12, further comprising a hydrogel coating deposited over the foam.

14. A device as recited in claim 10, wherein the expandable reservoir comprises a hollow tube having a first end fluid coupled to the channel in the insert tube and an opposing second end, the second end being flattened and coiled in a resting position.

15. A device as recited in claim 10, wherein the sealing means comprises a flexible flange radially outwardly extending from the proximal end of the insert tube to an outside edge.

16. A device as recited in claim 15, further comprising an O-ring mounted to the outside edge of the flange.

17. A device as recited in claim 10, further comprising one-way valve means for enabling fluid to travel from the channel to reservoir but preventing fluid from traveling from the reservoir to the channel.

18. A device for collecting involuntary urine flow through a urethra having an opening and a sphincter muscle, the device comprising:
   (a) an insert tube having a channel extending from free distal end to an opposing proximal end, the insert tube being sufficiently flexible to substantially collapse the channel under constriction of the sphincter muscle;
   (b) an opening on the insert tube extending from the exterior to the channel;
   (c) a flange radially outwardly extending from the proximal end of the insert tube; and
   (d) a reservoir tube having a first end fluid coupled to the insert tube and an opposing second end, the second end being coiled closed in a resting position.

19. A device as recited in claim 18, wherein the opening is positioned between the urethra opening and the sphincter muscle when the insert tube is inserted within the urethra.

20. A device as recited in claim 18, further comprising a plurality of opening extending from the exterior to the channel.

21. A device as recited in claim 18, further comprising means for manually uncoiling the reservoir tube.

22. A device for collecting involuntary urine flow through a urethra having an opening and a sphincter muscle, the device comprising:
   (a) an elongated insert having a free distal end and an opposing proximal end, the insert being configured for positioning within the urethra;
   (b) sealing means positioned at the proximal end of the insert for sealing the opening to the urethra closed when the insert is received within the urethra;
   (c) reservoir means attached to the sealing means on the side opposite the insert for holding fluid, the reservoir means comprising a reservoir tube having a chamber with a first end coupled to the fluid passageway;
   (d) a fluid passageway extending from the insert to the reservoir, the fluid passageway communicating with the exterior through an opening in the insert; and
   (e) valve means for selectively opening or closing external access to the chamber of the reservoir tube, the valve means comprising a second end of the reservoir tube being flattened and coiled.

* * * * *